United States Patent
Nurmela et al.

(10) Patent No.: US 9,311,808 B2
(45) Date of Patent: Apr. 12, 2016

(54) MONITORING SYSTEM

(71) Applicant: SENIORTEK OY, Rovaniemi (FI)

(72) Inventors: Pasi Nurmela, Rovaniemi (FI); Sami Nurmela, Rovaniemi (FI)

(73) Assignee: SENIORTEK OY, Rovaniemi (FI)

(*) Notice: Subject to any disclaimer, the term of this patent is extended or adjusted under 35 U.S.C. 154(b) by 0 days.

(21) Appl. No.: 14/390,558

(22) PCT Filed: Apr. 3, 2013

(86) PCT No.: PCT/FI2013/050363
§ 371 (c)(1),
(2) Date: Oct. 3, 2014

(87) PCT Pub. No.: WO2013/150187
PCT Pub. Date: Oct. 10, 2013

(65) Prior Publication Data
US 2016/0019774 A1    Jan. 21, 2016

(30) Foreign Application Priority Data
Apr. 4, 2012  (FI) .................................... 20125385

(51) Int. Cl.
*G08B 23/00* (2006.01)
*G08B 21/22* (2006.01)
(Continued)

(52) U.S. Cl.
CPC .............. *G08B 21/22* (2013.01); *A61B 5/1117* (2013.01); *G08B 21/0423* (2013.01); *G08B 21/0438* (2013.01); *G08B 25/016* (2013.01); *H04W 84/18* (2013.01)

(58) Field of Classification Search
CPC .... A61B 5/4094; A61B 5/1117; G08B 21/22; G08B 21/0423; G08B 25/016

USPC ..................... 340/573.4, 573.1, 506; 600/595
See application file for complete search history.

(56) References Cited

U.S. PATENT DOCUMENTS

| 5,905,436 A | 5/1999 | Dwight et al. |
| 6,462,663 B1 | 10/2002 | Wilson et al. |

(Continued)

FOREIGN PATENT DOCUMENTS

| AU | 2006319060 B2 | 11/2010 |
| DE | 112006003259 T5 | 11/2008 |

(Continued)

OTHER PUBLICATIONS

Zhang et al., "Design of an Unobtrusive Wireless Sensor Network for Nighttime Falls Detection," 33rd Annual International Conference of the IEEE EMBS, Aug. 30-Sep. 3, 2011, pp. 5275-5278.

*Primary Examiner* — John A Tweel, Jr.
(74) *Attorney, Agent, or Firm* — Birch, Stewart, Kolasch & Birch, LLP

(57) ABSTRACT

A monitoring device of a monitoring system includes a control, an alarm, a first sensor for detecting motion higher than a first predetermined height, a second sensor for detecting, on a floor of a building, motion lower than a second predetermined height, and a third sensor means for detecting an arrival in a sleeping place and a departure from the sleeping place. When the most recent motion detection fed by the third sensor to the control is the arrival in the sleeping place, the control controls the alarm to give an alarm if a predetermined first delay, beginning at the arrival in the sleeping place, is filled before information about the departure from the sleeping place has been received from the third sensor. After the third sensor has detected the departure from the sleeping place, the control controls the alarm to give an alarm if the control receives no motion detections from the first sensor and the second sensor during a predetermined second delay.

15 Claims, 3 Drawing Sheets

Figure 1:
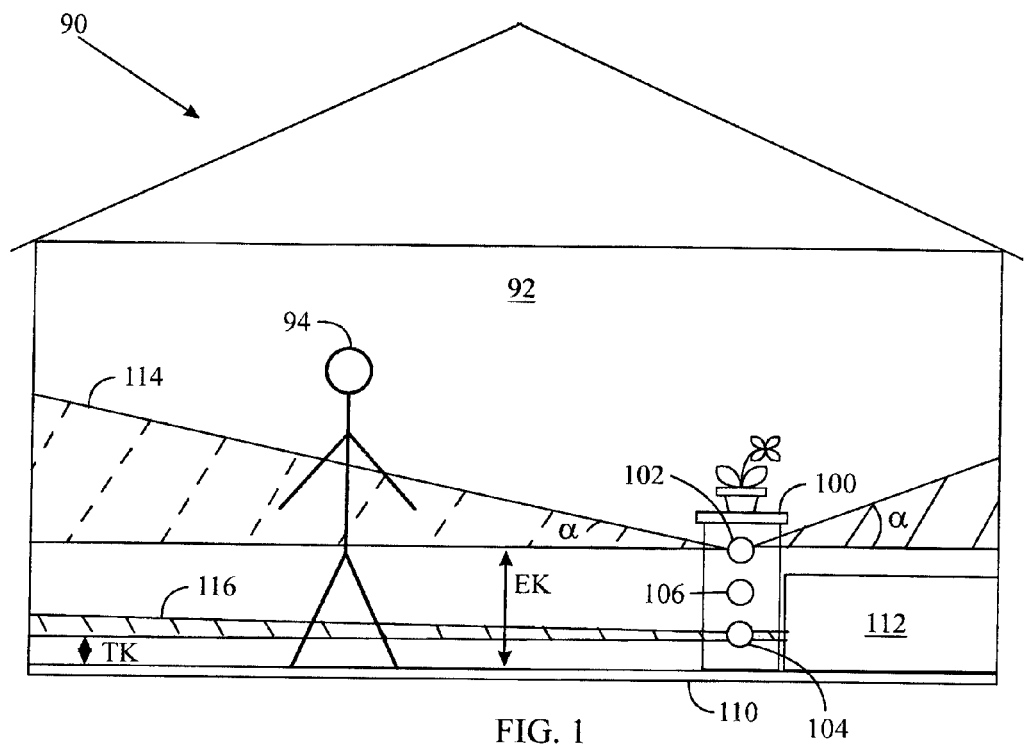

(51) Int. Cl.
*G08B 21/04* (2006.01)
*A61B 5/11* (2006.01)
*G08B 25/01* (2006.01)
*H04W 84/18* (2009.01)

(56) References Cited

U.S. PATENT DOCUMENTS

| | | | |
|---|---|---|---|
| 7,406,429 B2 | 7/2008 | Salonen | |
| 7,443,304 B2 * | 10/2008 | Rowe | G08B 21/22 340/573.4 |
| 7,567,200 B1 * | 7/2009 | Osterweil | G08B 21/22 340/573.1 |
| 7,610,208 B2 | 10/2009 | Salonen | |
| 7,657,279 B2 | 2/2010 | Lee et al. | |
| 7,782,215 B1 * | 8/2010 | Knapp, Jr. | G08B 21/22 340/573.4 |
| 7,912,190 B2 | 3/2011 | Salonen | |
| 8,026,820 B2 * | 9/2011 | Nurmela | G08B 21/0423 340/573.4 |
| 8,035,526 B2 * | 10/2011 | Needham | G08B 21/22 340/573.1 |
| 8,050,664 B2 | 11/2011 | Salonen | |
| 8,068,051 B1 * | 11/2011 | Osterweil | A61B 5/1117 340/573.1 |
| 8,115,641 B1 * | 2/2012 | Dempsey | G08B 21/0492 340/573.4 |
| 8,164,444 B2 * | 4/2012 | Anderson | G08B 21/22 340/539.11 |
| 8,334,778 B2 * | 12/2012 | Needham | G08B 21/22 340/573.1 |
| 8,593,279 B2 * | 11/2013 | Dreuillet | G08B 21/22 340/541 |
| 2007/0132558 A1 | 6/2007 | Rowe et al. | |
| 2011/0131286 A1 | 6/2011 | Salonen | |
| 2011/0173017 A1 | 7/2011 | Salonen | |
| 2011/0281595 A1 | 11/2011 | Salonen | |
| 2012/0063440 A1 | 3/2012 | Seo | |
| 2012/0158590 A1 | 6/2012 | Salonen | |

FOREIGN PATENT DOCUMENTS

| | | |
|---|---|---|
| EP | 1939770 A1 | 7/2008 |
| EP | 1955557 A1 | 8/2008 |
| EP | 1546938 B1 | 11/2008 |
| EP | 2014112 A1 | 1/2009 |
| EP | 2014113 A1 | 1/2009 |
| EP | 2301206 A1 | 9/2010 |
| EP | 2360603 A1 | 8/2011 |
| EP | 2369499 A1 | 9/2011 |
| EP | 2369500 A1 | 9/2011 |
| EP | 2381371 A1 | 10/2011 |
| FI | 117663 B | 12/2006 |
| FI | 118585 B | 12/2007 |
| FI | 118586 B | 12/2007 |
| GB | 2446965 B | 8/2010 |
| JP | 2007-325975 A | 12/2007 |
| JP | 4607585 B2 | 1/2011 |
| JP | 5159825 B2 | 3/2013 |
| RU | 2438267 C2 | 12/2011 |
| WO | WO 2004/019223 A1 | 3/2004 |
| WO | WO 2007/063179 A1 | 6/2007 |
| WO | WO 2007/065970 A1 | 6/2007 |
| WO | WO 2007/125171 A1 | 11/2007 |
| WO | WO 2007/125172 A1 | 11/2007 |
| WO | WO 2010/000949 A1 | 1/2010 |
| WO | WO 2010/103181 A1 | 9/2010 |
| WO | WO 2013/014578 A1 | 1/2013 |

* cited by examiner

MONITORING SYSTEM

FIELD

The invention relates to a system and method for monitoring a person in a building.

BACKGROUND

Movements of people suffering e.g. from dementia and mental disorders at home, in a hospital building, nursing home, service flat, departments or corresponding premises thereof can be monitored e.g. by means of a wristband to be worn round the wrist and able to be wirelessly connected by radio path with access control base stations attached to a building. A display provided in the system's control room may show a current state in the building, and the system may give an alarm if the person takes the wristband off or tries to leave without permission.

Since any equipment to be attached to a person is inconvenient and it is difficult by means of the above solution to detect e.g. if a person becomes immobile, solutions based on motion detection and pressure detection have been developed. When motion is monitored in a room occupied by a person, it is possible to detect if the person is immobile for too long. In such a case, it may be assumed that he or she has fallen, for instance, and an alarm is given. When a person's bed is provided with a pressure sensor, his or her dwelling in the bed may be monitored.

However, such a monitoring system presents problems. By motion detectors it is impossible to detect the actual instance of falling, but the assumption of falling is based on detecting no motion. This may cause unnecessary alarms and, in a real problem situation, too slow an alarm. The placement of the pressure sensor in the bed may interfere with the use of the bed, such as making and cleaning the bed. In addition, a large pressure sensor in particular may impede the person's sleep. Different positions of the person may also affect whether or not the person is detected to be in the bed. Further, if an object having the shape and/or weight of a human being placed in the bed, the system may assume that the person is in the bed even if this is not the case. Thus, a need exists to develop the monitoring system and the related monitoring method.

BRIEF DESCRIPTION

An object of the invention is to implement an improved monitoring system and monitoring method. This is achieved by a system according to claim 1.

The invention also relates to a method according to claim 8.

The invention further relates to a computer program according to claim 15.

Preferred embodiments of the invention are disclosed in the dependent claims.

The solutions according to the invention provide several advantages. A person's problem situations may be detected accurately, and an alarm may be carried out efficiently.

LIST OF FIGURES

Figure 2:
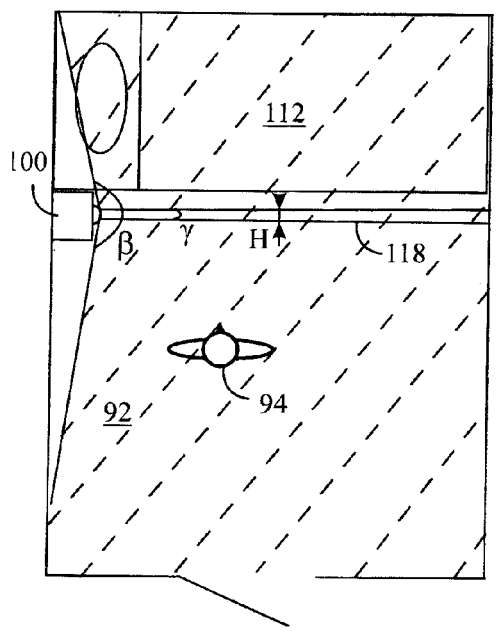
Figure 3:
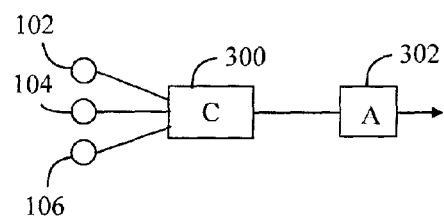
Figure 4:
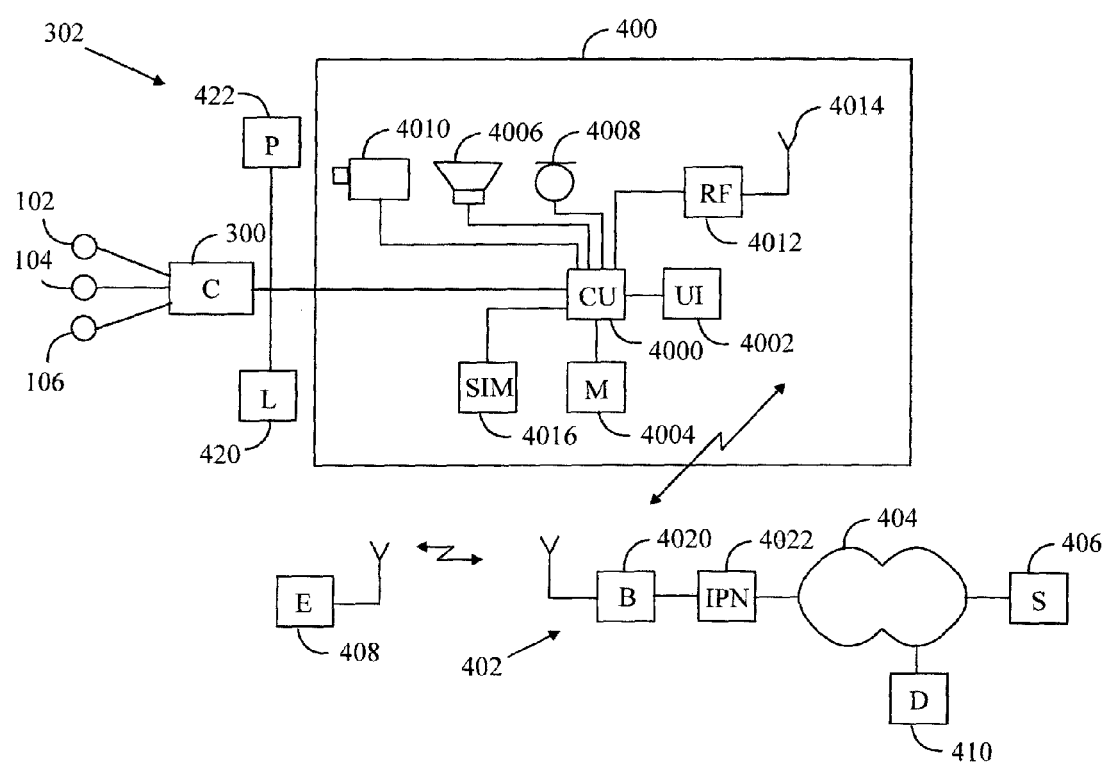
Figure 5:
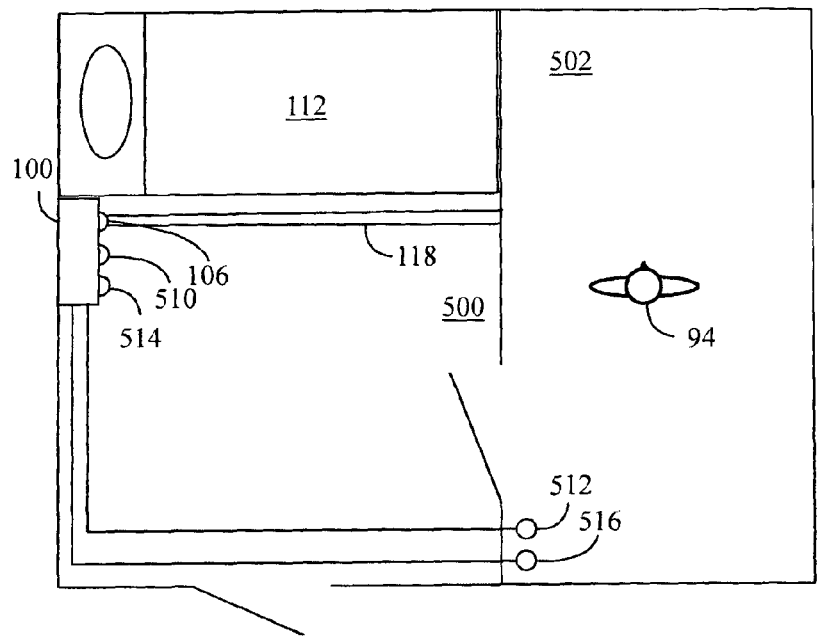
Figure 6:
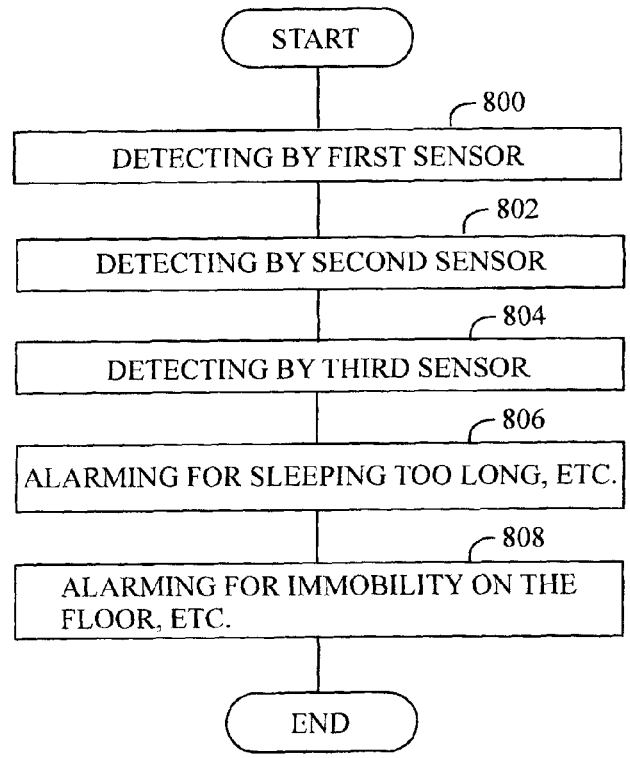

The invention is now described in closer detail in connection with preferred embodiments and with reference to the accompanying drawings, in which FIG. 1 is a side view of a monitoring device in a building,
FIG. 2 is a top view of a monitoring device in a building,
FIG. 3 is a block diagram of a monitoring device,
FIG. 4 is a block diagram of a monitoring system,
FIG. 5 shows a monitoring device when a person may be in two rooms, and
FIG. 6 is a flow chart of a method.

DESCRIPTION OF EMBODIMENTS

The following embodiments are presented by way of example. Even though the description may refer to "a", "one", or "some" embodiment or embodiments at different points, this does not necessarily mean that each such reference is made to the same embodiment or embodiments or that a feature only applies to one embodiment. Individual features of different embodiments may also be combined to enable other embodiments.

Let us first examine a monitoring device of a monitoring system by means of FIG. 1. In the solution according to FIG. 1, a building 90 contains one room 92 wherein one person 94 lives. In a general case, the number of rooms may be one or more and the number of persons may also be more than one. The building 90 may be the home of a private person, such as the home of the person 94 to be monitored, or a hospital building, a nursing home or the like. The monitoring device 100 comprises first sensor means 102 for detecting a person's 94 motion higher than a first predetermined height EK. The first predetermined height EK may be e.g. 0.3 m to 1.0 m, without, however, being restricted thereto. An angular aperture $\alpha$ of a first beam 114 formed by the first sensor means 102 may in a vertical direction be 0° to 90°. If the aperture is about 0°, the beam 114 is like an approximately flat plate at the first predetermined height EK. If, again, the aperture is 90°, the beam 114 fills up the entire room 92 higher than the first predetermined height EK. The monitoring device 100 also comprises second sensor means 104 for detecting motion occurring lower than a second predetermined height TK e.g. when crawling on a floor 110. The second predetermined height TK may be e.g. 0 m to 0.3 m, without, however, being restricted thereto. A second beam 116 formed by the second sensor means 104 may be a plate-like beam which fills up the entire room and whose thickness may range from a couple of centimeters to some tens of centimeters. The first predetermined height EK and the second predetermined height TK may be parallel, and an unmonitored space which is not included in the beams 114, 116 may be provided therebetween. The lowest height of the first predetermined height EK is always higher than the greatest height of the second predetermined height TK, so the first beam 114 and the second beam 116 do thus not overlap.

The monitoring device 100 further comprises third sensor means 106 for detecting an arrival in a sleeping place 112 and a departure from the sleeping place 112. A beam of the third sensor means 106 is narrow and located adjacent to the sleeping place 112 or otherwise in the immediate vicinity thereof. A diameter H of a beam 118 of the third sensor means 106 (FIG. 2) may be e.g. only tens of centimeters at most, often some centimeters only. The beam of the third sensor means 106 may extend across the room 92.

Let us now further examine the solution by means of FIG. 2. A horizontal angular aperture $\beta$ of the first sensor means 102 and the second sensor means 104 is wide, e.g. 180° or even more, in order to enable the entire room 92 to be covered. A horizontal angular aperture $\gamma$ of the third sensor means 106 is small, e.g. less than 10°, as is a vertical angular aperture as well, in order to enable such a beam 118 with a narrow diameter to be achieved.

The first, second and third sensor means 102, 104, 106 comprise motion detectors. In an embodiment, the motion detector may be a passive infrared sensor (PIR sensor), which detects infrared radiation generated by body heat. Such a motion detector may detect changes in the intensity of infrared radiation in different parts of the detecting surface of the detector when the person 94, i.e. the object emitting infrared radiation, moves within the area of the beam of the motion detector.

In an embodiment, the motion sensor may be an ultrasound detector, which emits ultrasound e.g. as bursts and receives reflected ultrasound. Such a motion detector is a kind of echo sounder, which can measure the ultrasound growing weaker and/or the time taken by reflection. When changes in these parameters within the area of the beam are detected, it may be interpreted that a moving object, e.g. the person 94, is within the area of the beam.

In an embodiment, the motion detector may be a microwave detector, which emits microwave region electromagnetic radiation but otherwise operates as the ultrasound detector. In an embodiment, the motion detector may also comprise two or more motion detectors of the same or different type.

The first and second sensor means 102, 104 detect motion inside a beam. The third sensor means 104, whose beam 118 has a narrow solid angle, are dimensioned to operate such that hitting the beam 118 is interpreted as arrival at the beam 118 but, in an embodiment, motion inside the beam 118 is not separately detected in any way.

Let us now examine the disclosed solution by means of FIG. 3. The monitoring device 100 comprises control means 300 which receive signals from the first, second, and third sensor means 102, 104, 106. The control means 300 may comprise information on a location permitted at a given time to the person 94 in the building 90. If the person 94 leaves the permitted location, no motion detection can be carried out on the person 94, which results in an alarm. In addition, e.g. by means of door sensors and/or sensors (camera, motion sensor, etc.) outside the permitted location it may be ensured that if the person 94 leaves the permitted location, an alarm will be given.

When the most recent motion detection fed by the third sensor means 106 to the control means 300 is the arrival in the sleeping place 112, i.e. the person 94 gets into the bed, the control means 300 control alarm means 302 to give an alarm if a predetermined first delay, beginning at the arrival in the sleeping place 112, is filled before information about the departure from the sleeping place 112 has been received from the third sensor means 106. The first delay may be a night. Thus, when the person 94 goes to bed to sleep and stays in the bed, no alarm is given during normal sleeping hours, which is represented by the first delay. However, an alarm is carried out if the person 94 does not get out of the bed during the first predetermined delay. The first predetermined delay is adjustable, but its value may be set e.g. to range from 1 h to 14 h. A motion detection means that the sensor means has detected that the person 94 moves. If the person 94 is immobile, it means no motion detection.

The control means 300 do not re-start the first predetermined delay if the person 94 departs from the sleeping place 112 in the middle of the first predetermined delay and the third sensor means 106 possibly detect this. Detections made by the first and second sensor means 102, 104 of movements of the person 94 in the first and second beam 114, 116 do not re-start the first predetermined delay, either, but the first predetermined delay may restart only after an already started first predetermined delay has elapsed. The length of the first predetermined delay may depend on the time of day. In the daytime, the length of the first predetermined delay may be e.g. 1 h to 3 h. By night, the length of the first predetermined delay may be e.g. 6 h to 14 h.

In an embodiment, when the third sensor means 106 have detected the departure from the sleeping place 112 and fed this information to the control means 300, the control means 300 control the alarm means 302 to carry out an alarm if the control means 300 receive no motion detections from the first sensor means 102 and the second sensor means 104 during a predetermined second delay. In the case of the second predetermined delay, the person 94 has thus come out of the bed and moved onto the floor 110. If he or she remains immobile on the floor 110 e.g. for minutes, a problem situation may be in question. Consequently, the second delay may be quite short, e.g. 1 min to 10 min. A long immobile period of the person 94 who has moved onto the floor may mean that he or she has fallen on the floor 110, for instance, and cannot get up. It is also possible that the person has fled. If after the departure from the sleeping place 112 motion is detected by the first and second sensor means 102, 104, the control means 300 do not control the alarm means 302 to give an alarm.

In an embodiment, after the third sensor means 106 have detected the departure from the sleeping place 112 and fed this information to the control means 300, the control means 300 control the alarm means 302 to give an alarm if the control means 300 receive no motion detections from the first sensor means 102 during a predetermined third delay even if the control means 300 do receive motion detections from the second sensor means 104 during the predetermined second delay. In such a case, the person 94 has got out of the bed, onto the floor 110 but is not in a vertical position even if he or she is moving. The person 94 may be e.g. looking for an object (e.g. spectacles or a watch) that has fallen on the floor 110. Consequently, the predetermined third delay may be longer than the predetermined second delay, e.g. 5 min to 30 min.

FIG. 4 shows a monitoring device even more closely. Each terminal 400, 408 comprises two parts: mobile equipment serving as an operational unit, whose radio frequency parts 4012 are used for establishing a radio connection to a network part 402, and a user-specific module or SIM (Subscriber Identity Module) 4016, which is a smart card comprising data about the identity of the subscriber and which typically carries out identification algorithms, stores encryption parameters and subscriber data.

The terminal 400 further comprises a processor 4000, i.e. one or more microprocessors for performing software functionalities of the terminal. The processor 4000 is responsible e.g. for digital signal processing, and controls the operation of other blocks. A user interface 4002 of the terminal may include a display and a keyboard, for instance. The terminal 400 is also provided with a memory 4004. The terminal 400 may further comprise a loudspeaker 4006, a microphone 4008, and a camera 4010. The radio frequency parts 4012, in turn, convert a signal to be transmitted, received from the processor 4000, into a radiofrequency signal so that it can be transmitted via an antenna 4014 as electromagnetic radiation. Similarly, a radiofrequency signal received by the antenna 4014 is converted to a lower frequency and digitized in the radio frequency part 4012 before the signal is fed to the processor 4000.

In an embodiment, the control means 300 and the processor 4000 are combined. In such a case, the computer program of the control means 300 is run on the processor 4000.

The radio system comprises a network part 402 and terminals 400, 408. The network part 402 includes base stations 4020, each comprising a transceiver for a radio connection to be carried out with the terminal 400, 408. The network part 402 also comprises an IP (Internet Protocol) node 4022 for transmitting messages between a data network 404 and the network part 402 of the radio system. The data network 404 may be the Internet, for instance.

A server 406 comprises both a computer and server software to be executed thereon which, in this application, executes e.g. said notification about the alarm to at least one predetermined device 408, 410 by email message, text message, and stores alarm data. The computer comprises a processor and a necessary amount of memory.

Let us now examine the operation of the system. The alarm device 302 may comprise a terminal 400 which, while an alarm is being given, is controlled by the control means 300 to wirelessly establish a connection via the radio system and the data network 404 to the server 406. In such a case, the terminal 400 may send an identification code, such as a telephone number, to the server 406. The server 406 may then, on the basis of the identification code it received, retrieve from its memory data about persons to whom an alarm from this identification code is to be sent. The identification code related to the start of an alarm may be associated with one or more predetermined telephone numbers and/or email addresses.

In an embodiment, the terminal 400 sends both its own telephone number and the predetermined one or more telephone numbers and/or email addresses to which the alarm is to be transmitted.

The server 406 may be a cloud server which notifies the alarm to at least one predetermined device 408, 410 by email message, text message, and stores the alarm data. The alarm data may comprise the identification code of the terminal 400 of the monitoring device 100, quality data about the alarm and/or data about to whom the alarm was transmitted, time of the alarm, etc.

The server 406 notifies the alarm to at least one predetermined device 408, 410 by email message, text message, and stores the alarm data. A text message may be sent by the server 406 via the data network 404 and the radio system to at least one predetermined terminal 408 which is a different terminal than the terminal 400 of the alarm means 302. An email message may be sent by the server 406 via the data network 404 to at least one predetermined other device 410, which may be a computer connected to the Internet. Both each predetermined terminal 408 and each predetermined other device 410 belong to predetermined people who are expected to help the person 94 with his or her problems. Often such predetermined people are the person's 94 relatives, but they may also be representatives of the treatment personnel, for instance. The person to be notified is thus the person monitoring the person 94 to be monitored who is most quickly or most efficiently capable of helping the person 94 to be monitored.

In an embodiment, the server 406 may receive from said one predetermined terminal 408 or other device 410 an acknowledgement of the email message, text message sent to said at least one predetermined terminal 408 or other device 410, and store the acknowledgement.

In an embodiment, the server 406 may send the telephone number of the terminal 400 of the monitoring device 100 to said at least one predetermined terminal 408, in which case said at least one predetermined other terminal 408 may establish a talking connection between the terminal 408 of the monitoring device 100. The user of the other terminal 408 selects the telephone number from the received text message, and calls it.

In an embodiment, the server 406 may send the telephone number of the terminal 400 of the monitoring device 100 to said at least one predetermined other device 410 for establishing a talking connection between the terminal of the user of the other device 410 and the terminal 400 of the monitoring device 100. In such a case, too, the user of the terminal starts a talking connection by entering via the user interface the received telephone number into the terminal and calling the terminal 400 of the monitoring device 100. Since the terminal 400 of the monitoring device 100 is provided with a loudspeaker 4006 and a microphone 4008, it is possible that the person 94 to be monitored answers when being called. If he or she answers; he or she may tell if he or she really needs help or what kind of help he or she needs. If he or she does not answer, the person who made the call may go and check the situation in situ and/or alarm someone else to go and help. In addition, in connection with the call the camera 4010 may send footage of the person 94 to be monitored and/or the room 92 where he or she is. This enhances the chances of the person making the call to assess the criticality of the alarm.

In an embodiment, the terminal 400 of the monitoring device 100 may send the server 406 data which depends on the sensor means 102, 104, 106 that have affected the alarm, and/or on a predetermined delay (first, second, third predetermined delay) which is associated with giving the alarm. The server 406 may communicate said data to said terminal of the at least one predetermined person or the device 408, 410. This clarifies the problem which caused the alarm and thus makes helping, if necessary, more efficient.

In an embodiment, the server 406 sends information about the first person to reply to and acknowledge the alarm transmitted by the server 406 to the rest of the predetermined devices 408, 410. Thus, the other monitoring persons know who takes care of the procedures relating to the alarm.

In an embodiment, the control means 300 may switch on the terminal 400 of the monitoring device 100 in connection with an alarm and switch off the terminal 400 of the monitoring device 100 after a predetermined delay set for the terminal 400 has elapsed. The predetermined delay set for the terminal 400 may be e.g. 5 min to 1 h. The switching on and off of the entire terminal 400 of the monitoring device 100 may be directed at the radio frequency parts 4012 of the terminal 400. In such a case, the terminal 400 of the monitoring device 100 may operate in other respects but cannot be used as an actual terminal since it cannot receive or send messages. Such keeping the radio frequency parts or the entire terminal switched off when no alarm is in question protects the person 94 to be monitored against unnecessary and possibly harmful contacts.

In an embodiment, the server 406 may provide said at least one predetermined device 408, 410 with alarm location data, which is based on the identification code of the terminal 400 of the monitoring device 100 and on the fact that the monitoring device 100 is stationary. The location data, which may comprise an address, may be displayed on a map, for instance. In addition, said at least one predetermined device 408, 410 may be provided with driving instructions. Herein, satellite positioning and/or Internet map services may be utilized, for instance.

The server 406 and the communication between the server 406, the terminal 400 of the monitoring device 100 and at least one other terminal 408 may be based on BookIT DDM (Dynamic Dialogue Matrix) smart text message application known per se, whereto are related the following patents or patent applications: U.S. Pat. No. 7,406,429; U.S. Pat. No. 7,610,208; U.S. Pat. No. 7,912,190; U.S. Pat. No. 8,050,664; U.S. Ser. No. 10/734,352; U.S. Ser. No. 12/226,876; U.S. Ser. No. 12/226,878; U.S. Ser. No. 12/401,392; U.S. Ser. No. 12/944,749; U.S. Ser. No. 12/958,870; U.S. Ser. No. 12/972,610; U.S. Ser. No. 13/002,512; U.S. Ser. No. 13/039,338; U.S. Ser. No. 13/074,037; U.S. Ser. No. 13/332,409; EP 1546938; EP 06820097.1; EP 07730716.3; EP 07730717.1; EP 08153844.9; EP 09772636.8; EP 10177875.1; EP 10181591.8; EP 10181576.9; EP 10181603.1; PCT/FI 2003/000617; PCT/FI 2006/050517; PCT/FI 2007/050229; PCT/FI 2007/050230; PCT/FI 2009/050611; PCT/FI 2010/050176; DE 112006003259.3; GB 2446965; RU 2324221; RU 2008125803; SG 110328; FI 117663; FI 118585; FI 118586; FI 20085701; FI 20095238; NO 20082896; CN 03819821.5; CN 20068052298; HK 05110515.0; 2968/KOLNP/2007; 2980/KOLNP/2007; 2891/KOLNP/2007; JP 4607585; JP 2010-114075; AU 2006319060; ZA 2008/05693.

In an embodiment, the monitoring device 100 comprises an alarm signalling device 420, which may be a signalling light source or a signalling noise source. After an alarm has been given, the signalling device 420 may e.g. blink a light or give noise signals until the alarm has been replied.

In an embodiment, the monitoring device 100 comprises acknowledging means 422 by means of which the person who has come to the person 94 to be monitored may acknowledge the alarm, in which case all the automatic procedures associated with the alarm stop and the monitoring device 100 returns to its normal state. The acknowledging means 422 may be a separate push button or they may be part of the user interface 4002. The use of the acknowledging means 422 may be stored in the memory 4004 and/or on the server 406.

In an embodiment, the monitoring means 100 is connected to a fire alarm, carbon monoxide detector, moisture alarm and/or freeze alarm. The carbon monoxide detector alerts people to an excessive carbon monoxide content in the air. The moisture alarm alerts people to an increase in the moisture content of water distribution points if e.g. a water tap has been left open and water is running therefrom for too long. The freeze alarm gives an alert if the temperature in a room drops below a predetermined value. In addition, it may have as an additional feature that an alert is given only if the temperature stays below a predetermined value longer than for a predetermined period of time. If the fire alarm detects smoke and alerts the person 94, the control means 300 also control the terminal device 400 included in the alarm means 302 to give an alarm as disclosed above. At least one of the predetermined persons may thus alert the fire authorities.

An alarm may be given in a similar manner also when the carbon monoxide detector, moisture alarm and/or freeze alarm react to an abnormal situation. This means that some monitoring person will always check the situation and ensure that the problem will be taken care of appropriately.

In an embodiment, no server 406 is used or it is unavailable. In such a case, the control means 300, when an alarm is being given, may control the terminal 400 to establish a wireless connection via a mobile telephone system to at least one predetermined terminal 408 whose telephone number is stored in the memory 4004 of the terminal 400 of the monitoring device 100.

In an embodiment, the terminal 400 of the monitoring device 100 may send a predetermined text message to said at least one predetermined person in possession of the predetermined terminal 408.

In an embodiment, the terminal 400 of the monitoring device 100 may send a predetermined text message which depends on the sensor means 102, 104, 106 that affected the alarm and/or on a predetermined delay associated with giving the alarm.

Instead of one person 94 to be monitored, the number of persons to be monitored in the same room 92 may be more than one. Usually, the number of persons in the same room 92 is no more than two. In such a case, each person 94 may be provided with a separate sleeping place 112 of his or her own and third sensor means 106 in the vicinity thereof. This enables each person's 94 arrival in and departure from his or her sleeping place 112 to be monitored separately. Further, during the night in particular, people mostly move about unaccompanied, so the movements of a person gone to the toilet, for instance, may be monitored as in the case of one person.

FIG. 5 shows an embodiment where the person 94 has in his or her use several rooms 500, 502 that cannot be monitored by a monitoring device 100 provided in one frame. In such a case, the first sensor means 102 comprise first sensor means parts 510, 512 located in each room 500, 502. Similarly, the second sensor means parts 104 also comprise sensor means parts 514, 516 located in each room 500, 502. The third sensor means parts 106 may also be distributed to different rooms 500, 502 but usually no need exists for this because ordinarily a person 94 sleeps in one sleeping place 112 only. In a similar manner, even one room may be provided with several sensor means parts if the room contains shadow areas e.g. because of furniture when one sensor means part is used.

The control means 300 and/or the terminal 400 may comprise a computer comprising a processor and memory. Their operation is based on a sequence of program commands of the computer program controlling the operation, stored in the memory.

Instead of or in addition to using a processor and memory, controlling may be implemented as one or more integrated circuits, such as an application-specific integrated circuit ASIC. Other equipment embodiments are also feasible, such as a circuit constructed of separate logic devices. A hybrid of these different implementations is also possible.

FIG. 6 is a flow chart of a method. In step 800, the first sensor means 102 detect first motion higher than a predetermined height EK. In step 802, the second sensor means 104 detect, on the floor 110 of the building 90, motion lower than a second predetermined height TK. In step 804, the third sensor means 106 detect 804 an arrival in and a departure from a sleeping place 112. In step 806, when the most recent motion detection fed by the third sensor means 106 to the control means 300 has been the arrival in the sleeping place 112, the control means 300 control the alarm means 302 to give an alarm if a predetermined first delay, beginning at the arrival in the sleeping place 112, is filled before information about the departure from the sleeping place 112 has been received from the third sensor means 106. In step 808, the control means 300 control the alarm means 302 to give an alarm after the third sensor means 106 have detected the departure from the sleeping place 112 if the control means 300 have received no motion detections from both the first sensor means 102 and the second sensor means 104 during a predetermined second delay.

The method shown in FIG. 6 may be implemented as a logic circuit solution or computer program.

When the monitoring system comprises at least one processor and memory with a computer program, the computer program and the memory can, together with said at least one processor, cause the monitoring system to execute, as disclosed in the method: detecting 800 by the first sensor means 102 first motion higher than the predetermined height EK; detecting 802 by the second sensor means 104 on the floor 110 of the building 90 motion lower than the second predetermined height TK; detecting 804 by the third sensor means 106 the arrival in the sleeping place 112 and the departure from the sleeping place 112; controlling 806 by means of the control means 300 the alarm means 302 to give an alarm when the most recent motion detection fed by the third sensor means 106 to the control means 300 has been the arrival in the sleeping place 112 if the predetermined first delay, beginning at the arrival in the sleeping place 112, is filled before information about the departure from the sleeping place 112 has been received from the third sensor means 106; and controlling 808 by means of the control means 300 the alarm means 302 to give an alarm after the third sensor means 106 have detected the departure from the sleeping place 112 if the control means 300 have received no motion detections from both the first sensor means 102 and the second sensor means 104 during the predetermined second delay.

The computer program may be placed on a computer program distribution means for the distribution thereof. The computer program distribution means is readable by means of a data processing device, and it may encode the computer program commands to control the operation of the measuring device.

The distribution means, in turn, may be a solution known per se for distributing a computer program, for instance a computer-readable medium, a program storage medium, a computer-readable memory, a computer-readable software distribution package, a computer or a computer-readable compressed software package.

Even though the invention has been described above with reference to the examples according to the attached drawings, it is clear that the invention is not restricted thereto but may be modified in many ways within the scope of the accompanying claims.

The invention claimed is:

1. A monitoring system for monitoring a person in a building, wherein a monitoring device of the monitoring system comprises control means comprising information on a location permitted at a given time to the person in the building, alarm means, first sensor means for detecting motion higher than a first predetermined height, second sensor means for detecting, on a floor of the building, motion lower than a second predetermined height, and third sensor means for detecting an arrival in a sleeping place and a departure from the sleeping place;
   when the most recent motion detection fed by the third sensor means to the control means is the arrival in the sleeping place, the control means are configured to control the alarm means to give an alarm if a predetermined first delay, beginning at the arrival in the sleeping place, is filled before information about the departure from the sleeping place has been received from the third sensor means; and
   after the third sensor means have detected the departure from the sleeping place, the control means are configured to control the alarm means to give an alarm if
   the control means have received no motion detections from the first sensor means and the second sensor means during a predetermined second delay.

2. A system as claimed in claim 1, wherein after the third sensor means have detected the departure from the sleeping place, the control means are configured to control the alarm means to give an alarm if the control means have received no motion detections from the first sensor means during a predetermined third delay when the control means receive motion detections from the second sensor means during the predetermined second delay.

3. A system as claimed in claim 1, wherein the alarm means comprise a terminal whose control means, while an alarm is being given, are configured to control a wireless connection to be established via a mobile telephone system and a data network to a server configured to notify the alarm to at least one predetermined device, and store alarm data.

4. A system as claimed in claim 3, wherein the server is configured to receive from said one predetermined device an acknowledgement of a message sent to said at least one predetermined device and store the acknowledgement.

5. A system as claimed in claim 4, wherein the server is configured to send a telephone number of the terminal of the monitoring device to said at least one predetermined terminal for establishing, on the initiative of said at least one predetermined terminal, a talking connection between said at least one predetermined terminal and the terminal of the monitoring device.

6. A system as claimed in claim 3, wherein the terminal of the monitoring device is configured to send to the server information which depends on the sensor means that affected the alarm and/or on a predetermined delay associated with the alarm, and a cloud server is configured to notify said data to said at least one predetermined device.

7. A system as claimed in claim 3, wherein the control means are configured to switch on radio parts of the terminal of the monitoring device in connection with an alarm and to switch off said radio frequency parts after a predetermined delay set for the terminal.

8. A method of monitoring a person in a building, wherein a monitoring device of a monitoring system comprising control means which receive from first, second, and third sensor means motion-related signals, the method comprising:
   detecting by the first sensor means first motion higher than a predetermined height;
   detecting by the second sensor means, on a floor of the building, motion lower than a second predetermined height;
   detecting by the third sensor means an arrival in a sleeping place and a departure from the sleeping place;
   when the most recent motion detection fed by the third sensor means to the control means is the arrival in the sleeping place, the control means control alarm means to give an alarm if a predetermined first delay, beginning at the arrival in the sleeping place, is filled before information about the departure from the sleeping place has been received from the third sensor means; and
   controlling by the control means the alarm means to give an alarm after the third sensor means have detected the departure from the sleeping place if the control means have received no motion detections from both the first sensor means and the second sensor means during a predetermined second delay.

9. A method as claimed in claim 8, the method further comprising controlling by the control means the alarm means to give an alarm after the third sensor means have detected the departure from the sleeping place if the control means have received no motion detections from the first sensor means during a predetermined third delay when the control means receive motion detections from the second sensor means during the predetermined second delay.

10. A method as claimed in claim 1, the method further comprising controlling, while an alarm is being given, by the control means a terminal of the monitoring device, which is included in the alarm means, to establish a wireless connection via a mobile telephone system and a data network to a server which notifies the alarm to at least one predetermined device and stores alarm data.

11. A method as claimed in claim 10, the method further comprising receiving by the server from said one predetermined device an acknowledgement of a mail message sent to said at least one predetermined device and storing the acknowledgement.

12. A method as claimed in claim 11, the method further comprising sending by the server a telephone number of the terminal of the monitoring device to at least one predetermined terminal in order to establish, on the initiative of said at least one predetermined terminal, a talking connection between said at least one predetermined terminal and the terminal of the monitoring device.

13. A method as claimed in claim 10, the method further comprising sending by the terminal of the monitoring device to the server information which depends on the sensor means that affected the alarm and/or on a predetermined delay associated with the alarm, and notifying by the server said information to said at least one predetermined device.

14. A method as claimed in claim 10, the method further comprising switching on, by the control means, radio parts of the terminal of the monitoring device in connection with an alarm and switching off, by the control means, said radio frequency parts after a predetermined delay set for the terminal.

15. A computer software product, comprising encoded instructions which, when loaded to control means, form a computer process for controlling operation of the control means when the control means are designed to control at least one stage in an alarm process, wherein the computer process produces method steps according to claim 8.

* * * * *